United States Patent [19]

Nordfang et al.

[11] Patent Number: 5,543,502

[45] Date of Patent: Aug. 6, 1996

[54] PROCESS FOR PRODUCING A COAGULATION ACTIVE COMPLEX OF FACTOR VIII FRAGMENTS

[75] Inventors: Ole Nordfang, Hillerod; Mirella E. Rasmussen, Copenhagen, both of Denmark

[73] Assignee: Novo Nordisk A/S, Novo Alle, Denmark

[21] Appl. No.: 383,541

[22] Filed: Feb. 3, 1995

Related U.S. Application Data

[63] Continuation of Ser. No. 92,658, Jul. 14, 1993, abandoned, which is a continuation of Ser. No. 956,445, Oct. 2, 1992, abandoned, which is a continuation of Ser. No. 835,100, Feb. 11, 1992, abandoned, which is a continuation of Ser. No. 162,323, Feb. 23, 1988, abandoned, which is a continuation-in-part of Ser. No. 932,923, Nov. 19, 1986, abandoned, and a continuation of PCT/DK87/00080, Jun. 24, 1987, abandoned.

[30] Foreign Application Priority Data

Jun. 24, 1986 [DK] Denmark ................................ 2957/86

[51] Int. Cl.$^6$ ..................... A61K 35/14; G07K 1/107; G07K 14/755; C12P 21/04
[52] U.S. Cl. ........................................ 530/383; 435/69.6
[58] Field of Search ................................ 530/383, 829, 530/830; 435/69.6

[56] References Cited

FOREIGN PATENT DOCUMENTS 0052874  6/1982  European Pat. Off. .

OTHER PUBLICATIONS

Vehar et al. 1984 Nature 312:337–342.
Eaton et al. 1986 Prog Hemostas. Thromb 8:47–70.
Truett et al. 1988 DNA 4(5):333–349.
Siepes et al. 1982 "Protein Purification" 194–197.
Mikaelsson et al. Abstract No. 1012 and 0822 Thrombosis Haemostas 50(1) 1983.
Church et al (1984) Proc. Natl. Acad. Sci. 81, 6934–6937.
Fass et al. (1982) Biol. Abstr. 74,, No. 44255.
EP Search Report 5 Pages.

*Primary Examiner*—Mindy Fleisher
*Assistant Examiner*—Nancy J. Degen
*Attorney, Agent, or Firm*—Steve T. Zelson, Esq.; Cheryl H. Agris, Esq.

[57] ABSTRACT

A coagulation active complex of Factor VIII fragments is produced by causing a coagulation inactive FVIII heavy chain to react with a coagulation inactive FVIII light chain in the presence of a complex forming agent. Thus, FVIII-HC and FVIII-LC are converted to coagulation active FVIII complex in the presence of metal ions, such as $Mn^{2+}$, $Ca^{2+}$, or $Co^{2+}$ or a component of the prothrombin complex or a substance having reactivity to compounds containing the group —SH and/or —S—S.

5 Claims, No Drawings

PROCESS FOR PRODUCING A COAGULATION ACTIVE COMPLEX OF FACTOR VIII FRAGMENTS

This application is a continuation application of application Ser. No. 08/092,658, filed Jul. 14, 1993, now abandoned, which is a continuation application of application Ser. No. 07/956,445, filed Oct. 2, 1992, now abandoned, which is a continuation of application Ser. No. 07/835,100 filed on Feb. 11, 1992, now abandoned, which is a continuation of Ser. No. 07/162,323 filed on Feb. 23, 1988, now abandoned, which is a continuation-in-part of Ser. No. 06/932,923 filed on Nov. 19, 1986, now abandoned, and is a continuation of International Application PCT/DK87/00080 filed on Jun. 24, 1987, now abandoned.

The present invention concerns a process for producing a coagulation active complex of an N terminal fragment of Factor VIII with a molecular weight of 92 to 210 kd and a C terminal fragment of Factor VIII with a molecular weight of 80 to 70 kd.

Factor VIII is a protein occurring naturally in blood.

It participates as a cofactor in the conversion of FX to activated FX (FXa). The presence of FVIII increases the FXa generation rate about 200,000 times (Dieijen et al, J. Biol. Chem. 156, p. 3433, 1981). Lack of FVIII (hemophilia A) manifests itself as uncontrolled bleedings.

The role of FVIII in the coagulation cascade appears from the following scheme:

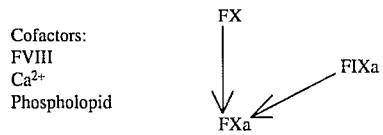

FVIII may be activated by thrombin or FXa and be inactivated by thrombin, FXa or protein C.

Hemophilia A patients are treated with FVIII preparations, either prophylactically or acutely in case of bleedings.

FVIII can be recovered from human blood plasma in which about 1 ppm of the protein is FVIII. This method can only produce limited amounts of FVIII, and it is therefore desirable to produce FVIII biosynthetically in cell culture. Three groups of researchers have been successful in doing this (Wood et al, Nature 312, p. 330, 1984—Toole et al, Nature 312, p. 342, 1984—Truet et al, DNA 4, p. 333, 1985).

2 mg of foreign protein/ml can be produced in cell culture. For FVIII this would correspond to 20,000 units/ml. This level far exceeds what has been described for FVIII in the literature. One of the reasons is that FVIII is a very large protein with a molecular weight of about 330 kd (Vehar et al, Nature 312, p. 337, 1984).

FVIII purified from blood plasma or from cell culture comprises a fragment called Factor VIII light chain or FVIII-LC with a molecular weight of about 80 kd, and a fragment called FVIII heavy chain or FVIII-HC with a molecular weight of from 92 to 210 kd. The fragments are produced from the 330 kd protein by proteolytic cleavage so that 80 kd FVIII-LC is the C terminal fragment, while FVIII-HC is the N-terminal fragment whose size depends upon the degree of cleavage.

Thus, it is known that coagulation active FVIII includes an 80 kd fragment and a fragment with a molecular weight of 92 kd or more (Fulcher and Zimmerman, Symposium on FVIII, Scripps Clinic, 1982).

It would be an advantage to produce FVIII from smaller fragments if these fragments in vitro could be combined to coagulation active FVIII. The fragments could more easily be produced biosynthetically in large amounts because of their smaller size with respect to intact FVIII. Further, the production of fragments of FVIII would be advantageous with a view to subsequent purification from cell culture as the product changes charge and molecular weight by the complex formation. Since it is thus possible to purify the fragments as well as the complex, a purer end product may be obtained.

Experiments have shown that simple combination of the fragments does not provide coagulation active products. Nor does the literature describe methods or conditions which would enable fragments of FVIII to be converted to a coagulation active complex.

The present invention is based on the finding that a coagulation active complex is produced when a coagulation inactive FVIII-heavy chain (FVIII-HC, N-terminal fragment) is caused to react with a coagulation inactive FVIII-light chain (FVIII-LC, C-terminal fragment) in the presence of a complex promoting agent. This is quite surprising because the literature reports purificiation of FVIII-LC and FVIII-HC, cf. DK Patent Application 5387/85, without reporting any attempted activity creating combination, notwithstanding that activity creation by combination might have great theoretical and practical importance.

Burke et al (Abstract 14 p. 111. Research in clinic and laboratory 16, 1986) have been able to produce coagulation active FVIII in vivo with cells transfected with DNA for both FVIII-LC and FVIII-HC. However, it was not possible to obtain coagulation activity by mixing culture supernatants which contained FVIII-LC and FVIII-HC, respectively, even though various conditions were tried.

FVIII-LC can be purified from human plasma and has no coagulation activity (see WO 86/02838). FVIII-HC fragments can also be purified from blood plasma (Truett et al, DNA 4, p. 333, 1985). Also these fragments are without coagulation activity.

According to the invention, one or more divalent metal ions are preferably used as complex promoting agents. Examples of suitable agents of this type are $Mn^{2+}$, $Ca^{2+}$ and $Co^{2+}$. Other suitable complex promoting agents are FIXa and FX and substances having reactivity to R—SH and/or R—S—S—R compounds. If desired, a mixture of these agents may be used.

DEFINITIONS

FVIII-LC or FVIII light chain is a fragment from the C terminal domain of full length FVIII. The molecular weight of the fragment is typically about 80 kd, but may be 70 kd or less. The fragment with the molecular weight of 80 kd has immunological reactivity in the described assay for FVIII-LC antigen and not in assay for FVIII-HC antigen.

FVIII-HC or FVIII heavy chain is a fragment from the N terminal domain of full length FVIII. The molecular weight of the fragment is typically 92 kd, but may be less and up to 210 kd. FVIII-HC purified from plasma consists of a mixture with a molecular weight of 92 to 210 kd. The fragment with a molecular weight greater than or equal to 92 kd has immunological reactivity in the described assay for FVIII-HC antigen but not in assay for FVIII-LC antigen.

Coagulation active FVIII is a protein which is capable of reducing the coagulation time of hemophilia A plasma in coagulation assay. Coagulation active FVIII is moreover capable of promoting the formation of FXa in Coatest assay (cf. the following) and thus of converting the chromogenic substrate. Coagulation activity is stated as FVIII:C.

Prothrombin complex is coagulation factors containing δ-carboxyglutamic acid, i.e. FII, FVII, FIX, FX protein C or activated forms of these coagulation factors (Davie et al, Advances in enzymology 48 p. 277, 1979).

METHODS

Coatest assay for FVIII:C

In this assay, FVIII:C is measured in a system consisting of FIXa, FX, $Ca^{2+}$ and phosphollpid (PL) (Rosen et al, Thromb Haemostas 54 p. 818, 1985). FXa is Formed in an amount depending upon the amount of FVIII:C. The assay is performed as indicated below:

Coatest assay for FVIII:C

1. A 50 µl sample is mixed with 50 µl of activation reagent (mixture of FIXa/FX and PL). Incubation time 10 min., 22° C.
2. 25 µl of 25 mM $CaCl_2$ is added, and the mixture is incubated For 20 minutes at 22° C.
3. 50 µl of chromogenic substrate (S2222) for FXa is added.
4. After incubation for 15 min. citric acid is added, and $E_{405}$ of the sample is read.

It is not possible in the Coatest assay to follow an enzymatic activation of FVIII because FVIII in the assay is activated fully by incubation with FIXa/FX, PL and $Ca^{2+}$.

Immunological quantization of FVIII-LC

FVIII-LC antigen (Ag) is measured in specific immunoassay (Nordfang et al, Thromb Haemostas 53, p. 346, 1985). Human inhibitor antibody is coated to microplates, sample is added, and bound FVIII-LC is detected with peroxidase labelled $F(ab')_2$ fragment of human inhibitor IgG. Normal human plasma is used as a standard.

Immunological quantization of FVIII-HC

FVIII-HC antigen (Ag) is measured in specific inhibition assay. Dog inhibitor antibody is coated to microplates with loose wells. Sample and $^{125}$I-labelled FVIII-HC are added. The amount of FVIII-HC in the sample determines the amount of bound $^{125}$I-FVIII-HC. The standard is FVIII concentrate (FVIII Nordisk) set to contain 1 FVIII-HC unit per FVIII:C unit.

The amount of FVIII-LC and FVIII-HC determined by immunoassay is stated relatively. That is the proportion between unit FVIII:C unit FVIII-LCAg unit FVIII-HCAg for various types of FVIII is not 1:1:1. However, it is assumed that units of the various assays are comparable, but there may be some difference between VIII:C unit, FVIII-LCAg unit and FVIII-HCAg unit for a FVIII sample in which all protein is coagulation active in Coatest.

Determination of molecular weight

Molecular weight is determined by reduced SDS-PAGE (Laemmli, Nature 227 p. 680, 1970).

Production of FVIII

FVIII sample for control tests was produced from FVIII concentrate (see WO 84/03628) by affinity chromatography on goat anti-von Willebrand Factor Sepharose (Truett et al, DNA 4 p. 333, 1985).

Preparation of FVIII-LC (sample A)

FVIII-LC may be purified from blood plasma by several methods (as described e.g. in WO 86/02838). Here, highly concentrated FVIII-LC is used, isolated by affinity chromatography on monoclonal 47 IgG of Nordiocto, produced as described by O. Nordfang et al.: Thrombosis and Haemostasis, Vol. 54, p. 586–590, 1985. Nordiocto, dissolved in 200 ml of buffer A (0.02M imidazole, 0.15M NaCl, 10 mM EDTA, pH 7.4) to a concentration of VIII-LCAg of 110 units/ml, was incubated overnight with 7 ml of 47 IgG sepharose (coupled with 9 mg of IgG/ml). The incubation mixture was poured on a column, and eluate was collected. The gel was washed with 40 ml of buffer A and 40 ml of buffer A with a total of 0.65M NaCl. FVIII-LC was eluted with 40 ml of 20 mM imidazole/0.65M NaCl/10 mM EDTA/50% ethylene glycol/pH 7.4. A peak fraction of 4 ml was dialysed to 50 mM imidazole/0.15M NaCl/10% glycerol/0.02% $NaN_3$/pH 7.4. The content of FVIII components in the dialysed sample appears from table 1.

Preparation of FVIII-HC (sample B)

FVIII-HC is produced from a FVIII sample by affinity chromatography on monoclonal 56 IgG Sepharose (produced as stated by O. Nordfang et al.: Thrombosis and Haemostasis, Vol. 54, p. 586–590, 1985. 56 IgG Sepharose binds the FVIII-LC/FVIII-HC complex via FVIII-LC. 25 ml of FVIII sample with a content of 405 FVIII-HCAg units/ml were incubated overnight with 1.5 ml of 56 IgG Sepharose (coupled with 4 mg of 56 IgG/ml). The incubation mixture was poured on a column, and eluate was collected. The gel was washed with 5 ml of buffer B (20 mM imidazole/0.15M NaCl/10% glycerol/0.1M lysine/pH 7.4) containing 0.35M $CaCl_2$. Then the gel was washed with 15 ml of buffer B with a total NaCl content of 0.65M followed by 5 ml of buffer B with 10 mM EDTA and 0.02% $NaN_3$ (EDTA buffer). The gel was drained and incubated for 1 hour at room temperature with EDTA buffer. After incubation, FVIII-HC was eluted with 5 ml of EDTA buffer. A peak fraction of 2 ml was dialysed to 50 mM imidazole/0.15M NaCl/10% glycerol/0.02% $NaN_3$/pH 7.4. The content of FVIII components in the dialysed sample appears from table 1.

TABLE 1

FVIII fragments in dialysed FVIII-LC sample and FVIII-HC sample

|  | FVIII:C unit/ml | FVIII-LCAg unit/ml | FVIII-HCAg unit/ml |
| --- | --- | --- | --- |
| FVIII-LC (sample A) | <0.01 | 770 | 1.8 |
| FVIII-HC (sample B) | <0.01 | 0.1 | 2000 |

Samples A and B were analysed by SDS-PAGE, see the attached figure, in which

Lane 1 corresponds to sample A (FVIII-LC) 4 FVIII-LCAg units,

Lane 2 contains molecular weight markers, and

Lane 3 corresponds to sample B (FVIII-HC) 8 FVIII-HCAg units.

The process of the invention will be illustrated below by means of some working examples.

EXAMPLE 1

Samples A and B were each diluted 10 times in buffer C (50 mM imidazole, 0.15M NaCl, 0.1% BSA, pH 7.4). 20 µl of A (diluted 1:10) was mixed with 20 µl of B 1:10, 3 µl of 0.15M $MnCl_2$ and 40 µl of buffer C. After 48 hours' incubation at 22° C. the incubation mixture contained 1200 m units of VIII:C/ml, measured by Coatest.

The following experiments were performed for comparison purposes

Experiment A:

The experiment was repeated as described in the example with the change that 3 µl of buffer C were added instead of 3 µl 0.15M $MnCl_2$. After 48 hours' incubation at 22° C., this incubation mixture contained less than 5 m units of VIII:C/ml, measured by Coatest.

Experiment B:

Sample A was diluted 40 times in buffer C. 80 μl of A (diluted 1:40) were mixed with 3 μl of 0.15M MnCl$_2$. After 48 hours' incubation, the incubation mixture contained less than 5 units of VIII:C/ml. Similarly, an incubation mixture with sample B contained less than 5 m units of VIII:C/ml.

Experiment C:

80 μl of FVIII sample diluted 1000 times in buffer C were mixed with 3 μl of 0.15M MnCl$_2$. After 48 hours' incubation 170 m units of VIII:C/ml were measured. 80 μl of FVIII sample diluted 1000 times in buffer C were mixed with 3 μl of buffer C. After 48 hours' incubation 140 m units of FVIII:C/ml were measured.

EXAMPLE 2

Samples A and B were each diluted 10 times in buffer C. 20 μl of A 1:10 were mixed with 20 μl of B (diluted 1/10), 3 μl of 2.2M CaCl$_2$ and 40 μl of buffer C. After 12 days' incubation at 22° C., the incubation mixture contained 1300 m units of VIII:C/ml.

The following experiment was performed for comparison purposes

The test was repeated as described above, but with the change that 3 μl of buffer C were added instead of 3 μl of 2.2M CaCl$_2$. After 12 days' incubation at 22° C., the incubation mixture contained less than 5 m units of VIII:C/ml.

EXAMPLE 3

Samples A and B were each diluted 100 times in buffer C. 100 μl of A and 100 μl of B were mixed. 50 μl of the mixture were tested in Coatest, as described above. 1.5 m units/ml were measured in the mixture. 50 μl of the mixture were moreover tested in modified Coatest with 1 hour's preincubation with FIXa/FX prior to addition of PL. Hereby, the Coatest activity increased to 3.0 m units/ml.

The following experiment was performed for comparison purposes

FVIII sample was diluted 30,000 times in buffer C. 50 μl of diluted sample were tested in Coatest, as described above. 3.4 m units/ml were measured.

50 μl of the diluted FVIII sample were moreover tested in modified Coatest with 1 hour's preincubation with FIXa/FX prior to addition of PL. 3.8 m units/ml were measured for the diluted FVIII sample.

EXAMPLE 4

When performing an experiment as described in example 1, 1000 m units of VIII:C/ml were measured after 24 hours' incubation. When 40 μl of FIXa/FX were added instead of 40 μl of buffer C, 1600 m units/ml were measured after 24 hours' incubation.

The following experiment was performed for comparison purposes

The experiment was performed as described in example 1, first comparison experiment. After 24 hours' incubation less than 5 m units/ml were measured in the incubation mixture. Another experiment for comparison purposes was performed as follows:

40 μl of FVIII sample diluted 500 times in buffer C were mixed with 40 μl of FIXa/FX and 3 μl of 0.15M Mn$^{2+}$. After 24 hours' incubation, 120 m units/ml were measured. When 40 μl of FIXa/FX were replaced by 40 μl of buffer C, 170 m units/ml were measured. When additionally the 3 μl of 0.15M Mn$^{2+}$ was replaced by of buffer C, 140 m units/ml were measured.

EXAMPLE 5

Samples A and B were each diluted 20 times in buffer C. 20 μl A 1/20 were mixed with 20 μl B 1/20, 40 μl FIXa/FX and 3 μl 0.15M CaCl$_2$. After 4 hours' incubation at 22° C. the incubation mixture contained 199 mU of FVIII:C/ml. If FIXa/FX in the mixture was replaced by 40 μl buffer C, then 43 mU of FVIII:C/ml were measured after 4 hours' incubation.

EXAMPLE 6

FVIII-LC and FVIII-HC samples containing 800 units of FVIII-LC:Ag/ml and 850 units of FVIII-HC:Ag/ml respectively, were each diluted 3 times. 20 μl of FVIII-LC 1/3 were mixed with 20 μl of FVIII-HC 1/3 and 10 μl of Me$^{2+}$. In mixture A, Me$^{2+}$ was 25 m Mn$^{2+}$. In mixture B, Me$^{2+}$ was 250 mM Ca$^{2+}$, and in mixture C, Me$^{2+}$ was 25 mM Mn$^{2+}$ and 250 mM Ca$^{2+}$. After 24 hours' incubation, mixture A contained 10.3 units of FVIII:C/ml, mixture B contained 4.0 units and mixture C contained 12.9 units of FVIII:C/ml. After 144 hours' incubation mixtures A, B and C contained 6.6 units, 6.5 units and 11.9 units of FVIII:C/ml, respectively.

EXAMPLE 7

COS cells were transfected with plasmid pSVF8-80 which expresses 80 kD chain, cf. DK Patent Application 0428/87. Supernatant from the culture containing 870 m units of FVIII-LC:Ag/ml was supplemented with plasma-purified FVIII-HC to a final concentration of 20 FVIII-HC:Ag units/ml and Mn$^{2+}$ to a final concentration of 5 mM. After 24 hours' incubation at 22° C. the mixture contained 137 m units of FVIII:C/ml. When plasma-purified FVIII-LC at a concentration of 1000 m units of FVIII-LC:Ag/ml was correspondingly supplemented with FVIII-HC and Mn$^{2+}$, the incubation mixture contained 33 m units of FVIII:C/ml after 24 hours' incubation. When the culture supernatant was supplemented with only Mn$^{2+}$ and not FVIII-HC, the mixture contained less than 2.5 m units of FVIII:C/ml after incubation for 24 hours.

EXAMPLE 8

25 μl of FVIII-LC were mixed in buffer C with 25 μl of FVIII-HC, 7 μl of MnCl$_2$ and 10 μl of redox agent to obtain end concentrations of the individual components as stated in table 2. FVIII:C was measured after 5 hours' incubation at 20° C.

TABLE 2

Recombination of FVIII-LC and FVIII-HC in the presence of a redox agent.

| FVIII-LC:Ag units/ml | FVIII-HC:Ag units/ml | mM MnCl$_2$ | Redox agent | % FVIII:C in relation to FVIII-LC:Ag after 5 hours |
|---|---|---|---|---|
| 11 | 11 | 5 | none | 4.9 |
| 11 | 11 | 5 | 15/uM DTT | 16.8 |
| 11 | 11 | 5 | 150/uM ME | 18.8 |
| 11 | 11 | 5 | 30/uM Cys | 17.4 |

TABLE 2-continued

Recombination of FVIII-LC and FVIII-HC in the presence of a redox agent.

| FVIII-LC:Ag units/ml | FVIII-HC:Ag units/ml | mM MnCl$_2$ | Redox agent | % FVIII:C in relation to FVIII-LC:Ag after 5 hours |
|---|---|---|---|---|
| 11 | 112 | 5 | 15/uM Cys | 68.8 |
| 11 | 11 | 0 | none | <0.5 |

At the stated concentrations of DDT (dithiotreitol), ME (mercapto ethanol) and Cys (Cystein), there is equilibrium between oxidizing and reducing form in aqueous buffer.

EXAMPLE 9

FVIII-HC was produced as described above and with the modification that EDTA elution buffer and dialysis buffer were mixed with 50 μm of mercapto ethanol. After dilution recombination with FVIII-HC samples was performed with 20 hours' incubation in buffer C at room temperature with addition of mercapto ethanol to 35 μM, MnCl$_2$ to 5 mM and FVIII-LC to 22 FVIII-LC:Ag units/ml.

TABLE 3

Table 3 shows recombination with the two FVIII-HC sample types.

| FVIII-HC | FVIII-HC:Ag units/ml in recombination mixture | % FVIII:C in relation to FVIII-HC:Ag after 20 hours |
|---|---|---|
| Sample 1, produced as described above | 2.59 | 31 |
| Sample 2, produced as described above | 3.31 | 27 |
| Sample 3, produced with ME as stated in this example | 3.00 | 89 |

EXAMPLE 10

An incubation mixture of the following composition was produced in buffer C from separated FVIII fragments: 60 units/ml of FVIII-LC, 60 units/ml of FVIII-HC, 50 mM CaCl$_2$, 2 units/ml of FX.

After 20 hours' incubation at room temperature, 6.9 FVIII:C units/ml were measured. In a corresponding incubation mixture without FX, 0.59 FVIII:C unit/ml was measured after 20 hours' incubation at 20° C.

We claim:

1. A process for producing a coagulation active complex comprising mixing a N-terminal isolated heavy chain fragment of Factor VIII having a molecular weight of 92 to 210 kD in which said heavy chain is treated with a substance having reactivity with a compound containing the group —SH or —S—S, a C-terminal isolated light chain fragment of Factor VIII having a molecular weight of 80 to 70 kD, and a complex promoting agent selected from the group consisting of at least one divalent metal ion, a component of the prothrombin complex, von Willebrand Factor, and a substance having reactivity to a component containing the group —SH or —S—S in a reaction medium.

2. A process according to claim 1, wherein the complex promoting agent is $Mn^{2+}$, $Ca^{2+}$, or $Co^{2+}$.

3. The process according to claim 1, wherein the N-terminal fragment has a molecular weight of about 92 kD and that the C-terminal fragment has a molecular weight of about 80 kD.

4. The process according to claim 1 wherein at least one fragment is produced biosynthetically.

5. The process according to claim 1 in which the isolated heavy chain fragment is treated with a substance having reactivity with a compound containing the group —SH and —S—S.

* * * * *